(12) United States Patent
Ishihara et al.

(10) Patent No.: US 8,084,266 B2
(45) Date of Patent: Dec. 27, 2011

(54) METHOD AND APPARATUS FOR SEPARATING ISOMERS OF CHIRAL SUBSTANCE

(75) Inventors: Hajime Ishihara, Sakai (JP); Takuya Iida, Sakai (JP); Hiroki Eguchi, Tokushima (JP)

(73) Assignees: Osaka Prefecture University Public Corporation, Osaka (JP); Japan Science and Technology Agency, Saitama (JP)

( * ) Notice: Subject to any disclaimer, the term of this patent is extended or adjusted under 35 U.S.C. 154(b) by 0 days.

(21) Appl. No.: 12/735,002

(22) PCT Filed: Dec. 12, 2008

(86) PCT No.: PCT/JP2008/072680
§ 371 (c)(1),
(2), (4) Date: Jun. 9, 2010

(87) PCT Pub. No.: WO2009/075359
PCT Pub. Date: Jun. 18, 2009

(65) Prior Publication Data
US 2010/0256354 A1  Oct. 7, 2010

(30) Foreign Application Priority Data
Dec. 13, 2007  (JP) .................................. 2007-322384

(51) Int. Cl.
*C07D 487/22*  (2006.01)
*C07D 487/00*  (2006.01)
(52) U.S. Cl. ............ 436/164; 540/450; 540/1; 422/255; 422/119
(58) Field of Classification Search ................... 436/164; 422/119, 243, 255; 540/145, 1
See application file for complete search history.

(56) References Cited

U.S. PATENT DOCUMENTS 6,808,603 B1  10/2004  Nishino et al.
(Continued)

FOREIGN PATENT DOCUMENTS

JP  2003-200399  7/2003
(Continued)

OTHER PUBLICATIONS

Inaba et al.: "Optical Manipulation of CuCl Nanoparticles Under an Excitonic Resonance Condition in Superfluid Helium", Physica Status Solidi (b, vol. 243, No. 14, pp. 3829-3833) Published Oct. 11, 2006. Graduate School of Engineering Science, Osaka University.

(Continued)

*Primary Examiner* — Christine T Mui
(74) *Attorney, Agent, or Firm* — Harness, Dickey & Pierce, P.L.C.

(57) ABSTRACT

In order to realize a method and an apparatus, each of which requires no contact treatment and no chemical reaction, for separating isomers of a chiral substance by irradiating a chiral substance with light such as circularly polarized light, so as to separate isomers in accordance with a difference in acceleration between the isomers, separation of isomers of a chiral substance in accordance with at least one embodiment of the present invention includes: (i) a circularly polarized light irradiating apparatus for irradiating, with circularly polarized light, a chiral substance which is a mixture of different isomers and is released from a molecular beam generating apparatus in a vacuum chamber; and (ii) isomer inlets for separating the different isomers of the chiral substance in accordance with a difference in acceleration between the different isomers.

13 Claims, 11 Drawing Sheets

U.S. PATENT DOCUMENTS

| | | | |
|---|---|---|---|
| 7,001,526 B1 * | 2/2006 | Tin | 210/745 |
| 2002/0050476 A1 * | 5/2002 | Ma et al. | 210/638 |
| 2007/0196937 A1 | 8/2007 | Itoh et al. | |
| 2008/0262240 A1 | 10/2008 | Kibar et al. | |
| 2009/0255807 A1 | 10/2009 | Itoh et al. | |

FOREIGN PATENT DOCUMENTS

| | | |
|---|---|---|
| WO | WO 2008/130980 | 10/2008 |

OTHER PUBLICATIONS

Sanchez-Castillo et al.: "Optical Circular Dichroism of Single-Wall Carbon Nanotubes", Physical Review B (vol. 73, 045401 (1-7)); Published Jan. 4, 2006. Instituto de Fisica.

Geremia et al.: Inorganic Chemistry Communication, "Assembly of Positively Charged Porphyrins Driven by Metal Ions: A Novel Polymeric Arrangement of Cationic Metalloporphyrin", (vol. 43, No. 24, pp. 7579-7581) Published on Web Oct. 28, 2004. Universita di Trieste.

Doki et al.: Crystal Growth and Design, "Simultaneous Crystallization of D- and L-Asparagines in the Presence of a Tailor-Made Additive by Natural Cooling Combined with Pulse Heating", (vol. 4, No. 6, pp. 1359-1363) Published on Web Oct. 13, 2004. Iwate University.

Ito et al.: Applied Physics Letters, "Laser Manipulation and Fixation of Single Gold Nanoparticles in Solution at room Temperature", (vol. 80, No. 3, pp. 482-484) Published Nov. 14, 2001. Osaka University.

Mori et al.: "Development of a Program to Estimate Dye-Configurations in Chirogenic Porphyrin Ensembles from UV-Vis. And CD Spectra", (J. Comput. Chem, vol. 4, No. 3 pp. 107-118) 2005, Tokyo University of Science (Partial English Translation).

Goda et al.: "Theory of Coupling Control of Magnetically-Induced Vortices in Multiple One-Dimensional Microstructures", Meeting Abstracts of the Physical Society of Japan (vol. 63, Issue 2, Part 4, pp. 583-898) Sep. 20-23, 2008. Iwate University (Partial English Translation).

Ishihara: "Excitation Property in Molecular Array Composed of Circular Ring Units", Meeting Abstracts of the Physical Society of Japan (vol. 63, Issue 1, Part 4, pp. 655-962) Mar. 22-26, 2008. Kinki University (Partial English Translation).

Eguchi et al.: "Theory of Resonant Radiation Force on an Organic Molecule with Chirality by Circular Polarized Light", Proceedings of the $18^{th}$ Symposium of Association for Condensed Matter Photophysics, 2007. (pp. 171-174) Osaka Prefecture University (Full English Translation).

Eguchi et al.: "Theory of Resonant Radiation Force on a Helical Nanostructure by Circular Polarized Light", (pp. 162-165) Proceedings of the $19^{th}$ Symposium of Association for Condensed Matter Photophysics, 2008. Osaka Prefecture University (Full English Translation).

European Search Report dated Mar. 16, 2011 EP Application No. 08859898.2.

Eguchi et al.: "Theory of Optical Manipulation of Chiral Molecules by Resonant Circular Polarized Light", Osaka Prefecture University (Full English Translation), Sep. 11, 2008.

* cited by examiner

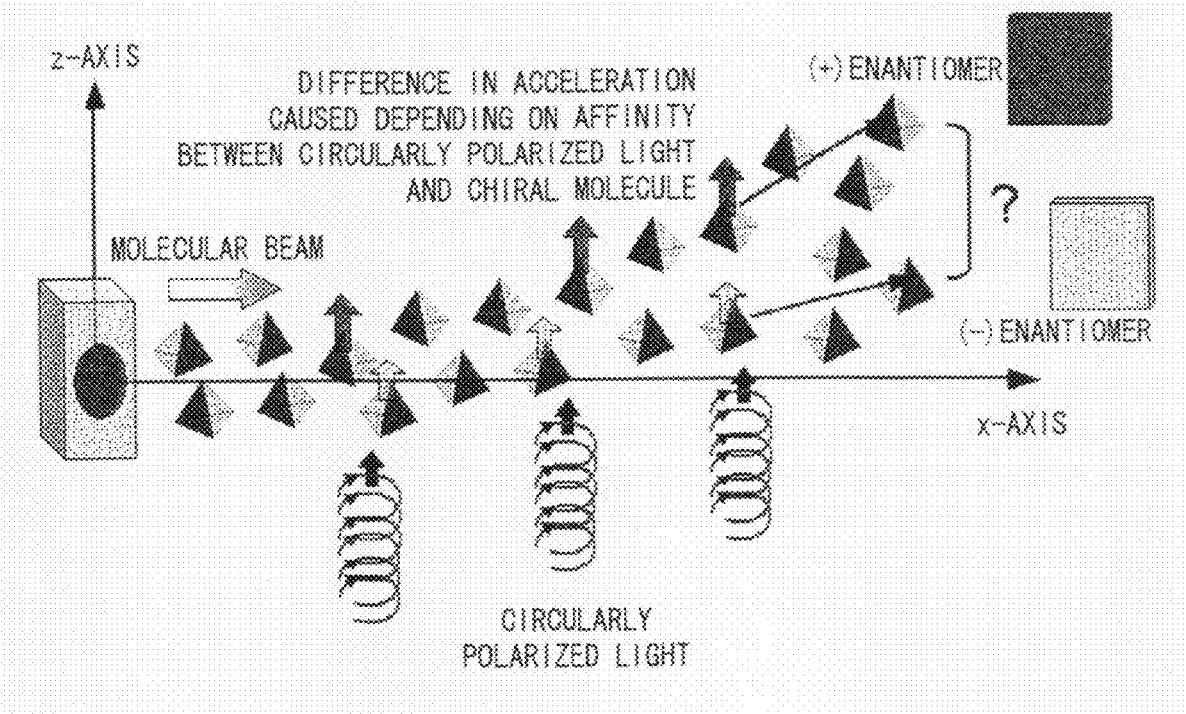

F I G. 1 2 (a)
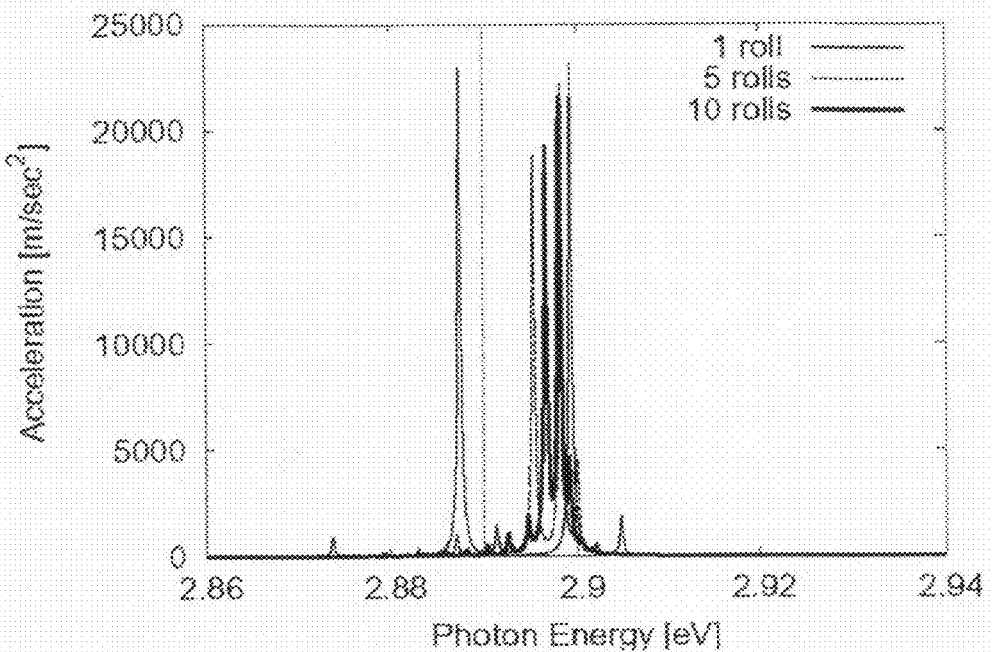
F I G. 1 2 (b)
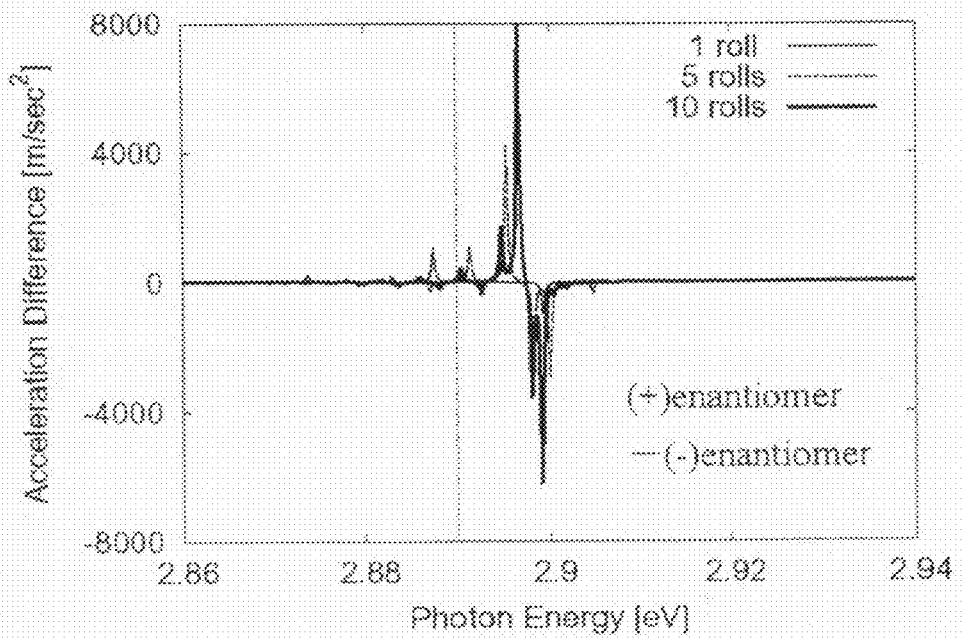

METHOD AND APPARATUS FOR SEPARATING ISOMERS OF CHIRAL SUBSTANCE

TECHNICAL FIELD

The present invention is related to a method and an apparatus for separating isomers of a chiral substance by: irradiating the chiral substance with light such as circularly polarized light, so as to cause a difference in radiation force between the isomers; and separating the isomers in accordance with a difference in acceleration between the isomers.

BACKGROUND ART

A substance whose real and mirror images cannot overlap is referred to as a "chiral" substance and a property thereof is referred to as "chirality". Many organic molecules and substances having helical structures have chirality due to their asymmetric steric structures, and isomers which are mirror images to each other exist therein.

Note that many of naturally-occurring polymers such as a protein, a sugar, and a nucleic acid consist of one of the isomers and carry out a function and a role which are essential for maintaining vital activities. Note also that enzymes which catalyze in-vivo reactions and main bodies of receptors which sense smell or taste are also proteins having chirality. In a case where a chiral substance for such a protein reacts instead of the protein, different biological activities will occur depending on which kind isomer the chiral substance is. However, in normal chemical synthesis, a chiral product is almost always synthesized as a racemate, and it is therefore important to selectively obtain one of the isomers from the viewpoints of pharmaceutical development, chemical industry, and the like.

In order to obtain only one of the isomers, activation energy produced in a reaction, a molecular mechanical kineticism, an intermolecular distance, and the like serve as important factors. In order to obtain only one of the isomers, it is conceivable to (a) control any of factors or (b) selectively apply power only to one of the isomers in a certain method so that the one of the isomers is transported to and extracted at a destination. However, it is difficult to control a molecule, which is frequently nanoscale.

On the other hand, there is a technique referred to as an optical manipulation for carrying out non-contact control with respect to a mechanical kineticism and a spatial arrangement of a micro substance by use of a radiation force (an emission force or a light pressure) caused by irradiating a substance with laser light. Note that this technique has conventionally been employed only for fields dealing with substances which have extremely different sizes such as laser cooling of an atom and research using optical tweezers for a substance existing in a trap or a micrometer range.

However, theoretical research has recently shown a new principle of the optical manipulation which allows selection of a nano substance whose size is intermediate between such extremely different sizes (refer to Patent Literature 1, for example). This optical manipulation of the new principle utilizes a variation in radiation force caused by irradiating the nanosubstance with electronically resonant light. Such variation of the radiation force reflects a quantum mechanical characteristic of the nanosubstance which quantum mechanical characteristic depends on a size, a form, an internal structure, and the like of the nanosubstance, individually. Particularly a recent study based on the theoretical suggestion tried manipulation in superfluid helium 4 by use of laser light which can induce electronic (excitonic) resonance to semiconductor particles. The study successfully obtained experimental data that suggests that the manipulation could transport an approximately several dozen nanometer particle for a macro distance of an order of several dozen centimeters (refer to Patent Literature 2 and Reference 1, for example). Inspired by the theoretical research, another group has also delivered an experimental report that by utilizing a gradient power caused by a focused beam that could induce near resonance, nano-sized organic polymers dispersed in a liquid at room temperature could stay longer in the vicinity of a focal point of a near-resonance-inducible light beam than in a case of non-resonance. This supports that a radiation force induced under resonant light irradiation is useful for a mechanical manipulation of a nanosubstance.

Note here that isomers are frequently substantially identical in physical and chemical property, except optical property. In particular, there can be found no difference in property between enantiomers for which only two kinds of isomers exist, except a difference in optical property such as optical rotatory power and circular dichroism. This makes it extremely difficult to selectively obtain only one of the enantiomers.

However, as described earlier, it is important to obtain only one of the enantiomers from pharmaceutical and chemical viewpoints, and thus a variety of methods for this purpose have been developed so far. Typical examples of the methods include: (i) an asymmetric synthesis method such that only one of the useful isomers is selectively synthesized by use of a chiral catalyst, (ii) an optical resolution method such that a racemate is produced and thereafter separated into the isomers, and (iii) a chiral pool method such that one of the isomers which is easy to obtain in a pure form is a starting material and is led to another chiral compound by a chemical conversion.

However, the asymmetric synthesis method which has been industrially employed as the most effective method these days faces such problems that: (i) no catalyst meeting requirements for the method has been found, (ii) a catalyst to be used is toxic and/or expensive, (iii) it is frequently technically difficult to separate a reaction product and a catalyst, or (iv) the like. Examples of the asymmetric synthesis method which has no such problem include an asymmetric autocatalytic reaction and an absolute asymmetric synthesis whose chiral source is circularly polarized light (refer to Patent Literature 3, for example). However, both these examples are limited in use. Further, the optical resolution method such as a crystallization method, a method employing a chemical chromatography, or an enzymatic method also has a problem such that: (i) it is difficult to establish the optical resolution method because the method varies depending on an object substance, (ii) an artificial manipulation such as a selection by use of a loupe and tweezers may be required, and (iii) the like. The chiral pool method also has a problem such that: (i) it is necessary to obtain a suitable starting material, (ii) the number of steps may increase, and (iii) the like.

Broadly speaking, all the methods above are similarly disadvantaged in (i) poor versatility and (ii) operational complexity. In view of the above circumstances, it is necessary to develop a new highly versatile method for separating enantiomers which makes it possible to concurrently (i) separate isomers from an isomeric mixture which is prepared in a simple manipulation by normal chemical synthesis or the like and (ii) evaluate a biological activity and the like of a chiral substance.

CITATION LIST

Patent Literature 1
Japanese Patent Application Publication, Tokukai, No. 2003-200399 A (Publication Date: Jul. 15, 2003)
Patent Literature 2
Pamphlet of International Publication, No. 05-087654 (Publication Date: Sep. 22, 2005)
Patent Literature 3
Japanese Patent Application Publication, Tokukai, No. 2001-131093 A (Publication Date: May 15, 2001)

SUMMARY OF INVENTION

The present invention has been made in view of the problems, and an object thereof is to provide a method and an apparatus, each of which requires no contact treatment and no chemical reaction, for separating isomers of a chiral substance by irradiating the chiral substance with light such as circularly polarized light so as to separate the isomers.

In order to attain the object, an isomer separation method for a chiral substance of the present invention, includes: irradiating the chiral substance which is a mixture of different isomers, with circularly polarized light or elliptically polarized light, so as to cause a difference in acceleration between the different isomers; and separating the different isomers in accordance with the difference in acceleration.

According to the arrangement, when the chiral substance is irradiated with the circularly polarized light or elliptically polarized light, there occurs a difference between the isomers in (i) absorbance obtained in absorbing this light and (ii) scattering. Then, such a difference in absorbance and scattering causes a difference in momentum obtained during a transition from a photon to the isomer, so that the isomers are different also in radiation force exerted on the respective isomers. This causes a difference in acceleration between the isomers themselves.

Subsequently, the isomers are separated in accordance with the difference in acceleration between the isomers. This makes it possible to realize a method, which requires no contact treatment and no chemical reaction, for separating isomers of a chiral substance.

In order to attain the object, an isomer separation apparatus for a chiral substance of the present invention, includes: circularly polarized light irradiating means for irradiating the chiral substance which is a mixture of different isomers, with circularly polarized light or elliptically polarized light; and isomer separating means for separating at least one of the different isomers from the chiral substance in accordance with a difference in acceleration between the different isomers of the chiral substance.

This allows realization of an apparatus, which requires no contact treatment and no chemical reaction, for separating isomers of a chiral substance.

For a fuller understanding of the nature and advantages of the invention, reference should be made to the ensuing detailed description taken in conjunction with the accompanying drawings.

BRIEF DESCRIPTION OF DRAWINGS

FIG. 7($b$), which shows the example of the present invention, is a graph illustrating a difference (in the z-axis direction) in acceleration applied to the respective enantiomers in the case where the porphyrin dimer is used.

FIG. 8($b$), which shows the example of the present invention, is a graph illustrating a difference (in the z-axis direction) in acceleration applied to the respective enantiomers in the case where the incident circularly polarized light rotates in the opposite direction to that illustrated in FIG. 6.

FIG. 9, which shows an example of the present invention, is a schematic view illustrating an example of a principle of an apparatus for separating enantiomers.

FIG. 10($b$), which shows the example of the present invention, is a graph illustrating a difference in distance flown by the respective enantiomers in the x-axis and z-axis directions, which difference is numerically calculated under the laboratory model for the enantiomer separation (250-time emission of circularly polarized light at regular intervals for a flight distance of 1 m, spot size of laser: 1 mm, initial velocity of molecular beam: 10 m/s).

FIG. 12($a$), which shows an example of the present invention, is a graph illustrating a photon energy dependence of an acceleration applied to a (+) enantiomer, which photon energy dependence is calculated under the model for the arrangement of the dipoles of the helical minute object (number of revolutions: 1, 5, and 10), assuming a cryogenic condition.

FIG. 12($b$), which shows the example of the present invention, is a graph illustrating a difference in acceleration applied to the (+) enantiomer and a (−) enantiomer, which difference is calculated under the model for the arrangement of the dipoles of the helical minute object (number of revolutions: 1, 5, and 10), assuming the cryogenic condition.

REFERENCE SIGNS LIST

Figure 1:
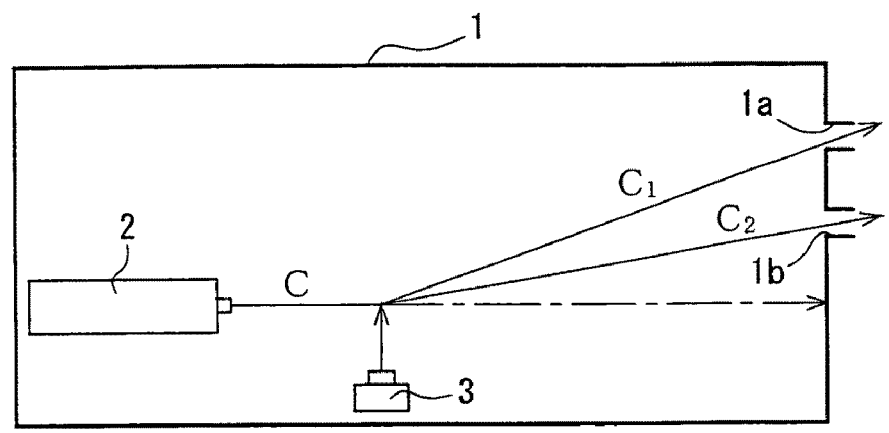
FIG. 1, which shows a first embodiment of the present invention, is a longitudinally sectional elevation view illustrating an arrangement of an apparatus for separating isomers of a chiral substance.

| | |
|---|---|
| 1 | Vacuum chamber |
| 1a | Isomer inlet |
| 1b | Isomer inlet |
| 2 | Molecular beam generating apparatus |
| 3 | Circularly polarized light irradiating apparatus |
| 4 | Cylindrical container |
| C | Chiral substance |
| $C_1$ | Isomer |
| $C_2$ | Isomer |

DESCRIPTION OF EMBODIMENTS

A preferred embodiment of the present invention is described below with reference to FIGS. 1 through 14.

A method for separating isomers of a chiral substance is such that: irradiation of a chiral substance with light such as circularly polarized light causes a difference in acceleration between different isomers of the chiral substance, and the different isomers are separated in accordance with this difference in acceleration. Further, an apparatus for separating isomers of a chiral substance is arranged such that: a circularly polarized light irradiating means irradiates the chiral substance with the light such as circularly polarized light, and isomer separating means separates the isomers.

A chiral substance refers to a substance which has chirality. The chirality is attributed to a molecular structure of the chiral substance in many cases. However, examples of the chiral substance also include a substance such as a carbon nanotube which results from a structure other than a molecular structure. A mixture of different isomers is used as this chiral substance because the object of the present invention is to separate isomers. Note here that examples of the isomers of the chiral substance include not only an enantiomer which consists of two isomers but also a diastereomer which consists of a plurality of isomers.

This chiral substance is preferably provided in a vacuum or a fluid medium such as a gas or a liquid so that the chiral substance is movable therethrough. Furthermore, it is preferably to set a pressure to not more than $10^{-3}$ Pa in the vacuum.

Moreover, this chiral substance may be static or movable in the vacuum or the fluid medium. Moreover, when being in the fluid medium, the chiral substance can move together with this fluid medium. In this case, however, it is preferable that a velocity component of the movement of the chiral substance is 0 (zero) if possible, or constant, in a direction in which the chiral substance is irradiated with light such as circularly polarized light.

It is preferable to irradiate the chiral substance with circularly polarized light so as to cause a large difference in acceleration between the isomers. Further, elliptically polarized light which can be represented by overlapping this circularly polarized light and linearly polarized light is also capable of causing a large difference in acceleration between the isomers.

The chiral substance is irradiated with the light such as circularly polarized light from a given direction. Furthermore, a moving chiral substance may be repeatedly or continuously irradiated with the light in an identical given direction from different places along a direction in which the chiral substance moves. Alternatively, the chiral substance may be irradiated with the light such as circularly polarized light from a plurality of different given directions. Note, however, that it is preferable to irradiate the chiral substance with left-handed or right-handed circularly polarized light or elliptically polarized light from the identical given direction. Note also that though it is possible to irradiate the chiral substance with left-handed and right-handed circularly or elliptically polarized light from different given directions, these given directions are preferably opposite, if possible, so that the isomers are greatly different in acceleration. Note that each of the given directions mentioned here is based on the direction in which the chiral substance moves. Therefore, for example, in a case where the chiral substance rotationally moves, inward radial directions are all identical given directions and outward radial directions are all identical given directions which are opposite to the inward radial directions.

When the chiral substance is irradiated with the light such as circularly polarized light, there occurs a difference between the isomers in (i) absorbance obtained in absorbing this light and (ii) scattering. Then, such a difference in absorbance and scattering causes a difference in momentum transferred from a photon to the isomer, so that the isomers are different also in radiation force. This causes a difference in acceleration between the isomers themselves.

The light such as circularly polarized light is not particularly limited in frequency. It is more preferable to use light having a frequency causing resonance at an electronic excitation level of any one of the isomers. This is because a difference in radiation force between the isomers is larger, if light having such a frequency is used. The light having such a frequency causing resonance at an electronic excitation level of an isomer may be light whose spectrum at least includes this frequency for resonance, and it is the most preferable that a maximum peak of the spectrum corresponds to this frequency for resonance. Moreover, light in which the frequency for resonance is included within full width at half maximum of this maximum peak is also sufficiently useful because the light has an intensity of not less than the half maximum of the maximum peak at this frequency for resonance. Note that the electronic excitation level refers to a quantum mechanical energy level of electrons included in a nanosubstance and the electronic excitation level discreetly exists in the nanosubstance. Note also that eigenenergy of the nanosubstance varies depending on its size, form, internal structure, and the like.

The light such as circularly polarized light for irradiating the chiral substance shall not be so intense or be emitted so long to break the chiral substance, since the object of the present invention is to separate the isomers. Note that the light such as circularly polarized light does not need to be laser light since the light does not need to have coherence (be coherent). However, the light is suitably laser light from which it is easy to sufficiently obtain an intensity and a light-focusing property. Accordingly, any light source is usable for circularly polarized light irradiating means. Examples of the light source include a Ti-Sapphire laser and a semiconductor laser. It is preferable to convert laser light emitted from the Ti-Sapphire laser or the semiconductor laser into circularly polarized light or elliptically polarized light by use of an optical device such as a polarizing device.

More specifically, in a case where a chiral substance which is to be manipulated is a porphyrin dimer, a laser light source is usable which emits light having a wavelength in a near-ultraviolet [near-UV] region where the porphyrin dimer is in an excited state, i.e., which emits light of approximately 2.9 eV (427 nm converted into wavelength). An example of the laser light source is a mode-locked Ti-Sapphire laser which serves as a tunable laser light source (fundamental: wavelength of 720 nm-900 nm, housing size: 812.8×310.9×192.0 mm). In this case, it is possible to set a wavelength of a second harmonic to 360 nm to 450 nm by use of a nonlinear optical crystal such as LBO or $LiO_3$ for the foregoing laser. It is also possible to use the semiconductor laser (center wavelength: 808 nm, wavelength: 780-980 nm, housing size: 44.2×40×25.6 mm) as the laser light source and to set a harmonic to a second one (center wavelength: 404 nm, wavelength: 390-490 nm). In particular, it is possible to miniaturize an apparatus by use of the semiconductor laser.

In order to separate isomers of a chiral substance in accordance with a difference in acceleration of the isomers, for example, it is possible to use displacement amounts of the isomers which displacement amount become different as time passes because the difference in acceleration causes the isomers to be different in speed at which the isomers are displaced. In a case where the chiral substance is static, the chiral substance starts moving when irradiated with light such as circularly polarized light. However, the isomers are different in movement speed, and this thus causes a difference between the isomers in movement distance (displacement amount) obtained after a given time. On the other hand, assume that the chiral substance is in linear motion. When irradiated with the light such as linearly polarized light from a direction which intersects with (may be "from a direction which is orthogonal to") a direction where the chiral substance is in linear motion, the chiral substance, which stays in linear motion, starts being displaced in a direction from which the chiral substance is irradiated. The isomers are different in speed at which the isomers are displaced as such, and this thus causes a difference between the isomers also in displacement amount obtained after a given time. Moreover, when the chiral substance, which is in linear motion, is irradiated with the light such as linearly polarized light from a direction which is parallel to a direction in which the chiral substance is in linear motion, there occurs a variation in speed at which the chiral substance is in linear motion. The isomers are different in variation in speed at which the isomers are displaced as such, and this thus causes a difference between the isomers also in position at which the isomers are located (displacement amount) obtained after a given time. Note that there occurs a difference in displacement amount between the isomers not only in a case where the chiral substance is in isokinetic linear motion. Assume that the chiral substance is in rotational motion. When irradiated with the light such as linearly polarized light from a direction which intersects with (may be "a direction of a rotation axis which direction is orthogonal to") a radius vector rotation plane of this rotation, the chiral substance in rotational motion starts being displaced in a direction from which the chiral substance is irradiated. The isomers are different in speed at which the isomers are displaced as such, and this thus causes a difference between the isomers also in displacement amount, that is, movement distance for which the isomers move in the direction of the rotation axis, obtained after a given time.

In a case where there occurs a difference in displacement amount between isomers as described above, by, for example, providing isomer inlets at positions corresponding to respective displacement amounts of the isomers, it is possible to capture only a given isomer through the corresponding isomer inlet thereby to separate the given isomer from another isomer. The isomer inlet is not particularly limited provided that at least one isomer inlet is provided. Furthermore, instead of providing such an isomer inlet, it is possible to provide (i) an apparatus or a substance which absorbs an isomer or substance (ii) a substance which (a) sticks to the isomer by adsorption or substance (b) chemically reacts with the isomer so as to collect the isomer from the substance (a) or (b). Moreover, according to the present invention, instead of providing such an isomer inlet, it is possible to provide a substance for detecting an isomer (isomer detecting means) so as to detect a property and/or a spatial position of the isomer by using such a substance. The term "separation" of isomers which is referred to in the present specification encompasses measurement, measuring, detection, and/or the like of separated isomers. Namely, examples of isomer separating means include: an inlet through which an isomer enters the isomer separating means, an apparatus for absorbing the isomer, an apparatus for detecting the isomer (an isomer detecting section), and a substance for absorption, adsorption, etc. of the isomer.

In particular, according to an arrangement in which an isomer detecting apparatus is provided, a chiral substance to be detected can be determined as to a composition and a property of an isomer thereof, whether or not the chiral substance contains a given isomer therein, or the other aspects of the chiral substance.

However, in a case where there occurs a variation only in speed of linear motion of a chiral substance, it is impossible to separate isomers only by where an isomer inlet or another apparatus or substance is provided. For this reason, for example, in a case where the isomer inlet is used, it is possible to control a timing for causing the isomer inlet to be open in such a manner that the isomer inlet is opened only when a target isomer reaches the isomer inlet, whereas the isomer inlet is closed when no target isomer reaches the isomer inlet. In this case, a difference in variation in speed between isomers due to a difference in acceleration between the isomers is used. Further, it is possible to separate isomers which are different in acceleration by providing, for example, an electrical barrier where an isomer comes and allowing only an isomer that has not less than a given speed or acceleration to cross this barrier.

According to the arrangement, it is possible to separate different isomers from a chiral substance which is a mixture of the different isomers. Furthermore, at least a separation process of this arrangement requires no contact treatment and no chemical reaction. Note that it is not always necessary to separate all isomers of a chiral substance but it is only necessary to partially separate the isomers (at least one or more) of the chiral substance.

Note that it has been conventionally been known that when a chiral substance is irradiated with circularly polarized light, there occurs a difference between isomers in (i) absorbance obtained in absorbing this light and (ii) scattering (e.g., circular dichroism). However, there has conventionally been no idea of using a difference in acceleration of isomers due to such a difference in absorbance and scattering. Otherwise though the difference occurring in acceleration may have been recognized, it has been considered that it is substantially impossible to take advantage of the difference, which is so imperceptible. However, the present invention has found that it is fully possible to use the difference in acceleration by elaborating a method of, for example, using light whose frequency causes resonance at an electronic excitation level or irradiating a chiral substance with left-handed and right-handed circularly polarized light from opposite directions. The present invention is directed to separate isomers in accordance with such a difference in acceleration.

First Embodiment

FIG. 1 illustrates a first embodiment of an apparatus for separating isomers of a chiral substance. A vacuum chamber 1 includes a molecular beam generating apparatus 2 and a circularly polarized light irradiating apparatus 3. The molecular beam generating apparatus 2 releases a beam of molecules of a chiral substance C. This chiral substance C is a mixture of two isomers $C_1$ and $C_2$ of an enantiomer. The chiral substance C released by the molecular beam generating apparatus 2 is in isokinetic linear motion in the vacuum chamber 1 from left to right (see FIG. 1).

The circularly polarized light irradiating apparatus 3 emits right-handed circularly polarized light which a polarizing device converts from laser light emitted from a semiconductor laser. This laser light has a frequency which causes resonance at an electronic excitation level of the isomer $C_1$ of the chiral substance C. The chiral substance C released by the molecular beam generating apparatus 2 is irradiated with the right-handed circularly polarized light emitted by the circularly polarized light irradiating apparatus 3 from below (see FIG. 1) in a direction which is orthogonal to a direction in which the chiral substance C is in isokinetic linear motion.

The vacuum chamber 1 is a container which is under vacuum inside. Isomer inlets 1a and 1b are vertically provided in an upper part of a side wall on the right-hand side of the vacuum chamber 1 (see FIG. 1). Assume that a point of the side wall of the vacuum chamber 1 with which point the chiral substance C released by the molecular beam generating apparatus 2 collides after the isokinetic linear motion (an intersection of a broken line drawn in FIG. 1 and the side wall on the right-hand side) is referred as a collision point. The inlets 1a and 1b are provided higher than this collision point.

When irradiated with no right-handed circularly polarized light emitted by the circularly polarized light irradiating apparatus 3, the chiral substance C released by the molecular beam generating apparatus 2 moves rightward in isokinetic linear motion in the vacuum chamber 1 and collides with the side wall on the right-hand side (see an arrow of a one-dot chain line).

However, in a case where this chiral substance C is irradiated, during the isokinetic linear motion, with the right-handed circularly polarized light emitted by the polarized light irradiating apparatus 3 from below, the chiral substance C is subjected to a vertically upward radiation force (see FIG. 1). This causes the chiral substance C to have an upward acceleration. Further, there is a difference between the isomers $C_1$ and $C_2$ of the chiral substance C in radiation force caused by the right-handed circularly polarized light. This also causes a difference in upward acceleration between the isomers $C_1$ and $C_2$. In addition, this right-handed circularly polarized light, which has a resonant frequency of the isomer $C_1$, further increases in radiation force. This causes the isomers $C_1$ and $C_2$ to be more different in acceleration.

For this reason, when the isomer $C_1$ is irradiated with the right-handed circularly polarized light which has a resonant frequency of the isomer $C_1$, the isomer $C_1$ greatly varies in movement direction so as to move upward. Therefore, the isomer $C_1$ is greatly displaced upward as it moves rightward. As a result, the isomer $C_1$ goes out of the vacuum chamber 1 through the isomer inlet 1a higher than the isomer inlet 1b on a side wall of the vacuum chamber 1. Then, the isomer $C_1$ is collected outside the vacuum chamber 1. On the other hand, when the isomer $C_2$ is irradiated with the right-handed circularly polarized light, the isomer $C_2$ slightly varies in movement direction so as to move upward. Therefore, the isomer $C_2$ is gradually displaced upward as it moves rightward. As a result, the isomer $C_2$ goes out of the vacuum chamber 1 through the isomer inlet 1b lower than the isomer inlet 1a on the side wall of the vacuum chamber 1. Then, the isomer $C_2$ is collected outside the vacuum chamber 1.

As a result, according to the apparatus of the present embodiment for separating isomers of a chiral substance, it is possible to separately extract the isomers $C_1$ and $C_2$ from the chiral substance C through their respective isomer inlets 1a and 1b which are vertically provided in the upper part of the vacuum chamber 1.

Second Embodiment

Figure 2:
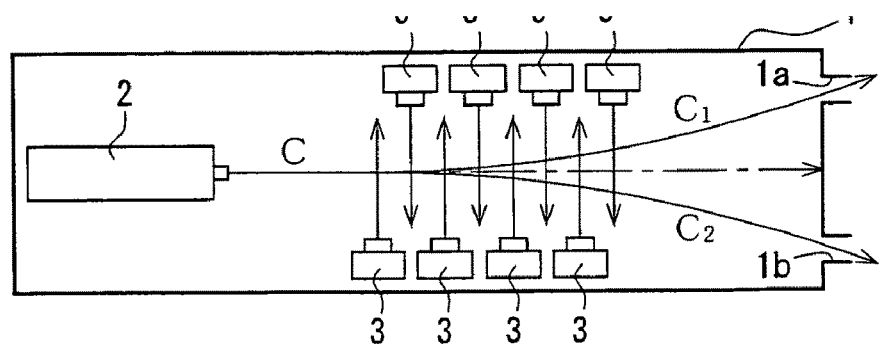
FIG. 2, which shows a second embodiment of the present invention, is a longitudinally sectional elevation view illustrating an arrangement of an apparatus for separating isomers of a chiral substance.

FIG. 2 illustrates a second embodiment of the apparatus for separating isomers of a chiral substance. A vacuum chamber includes a molecular beam generating apparatus 2 and circularly polarized light irradiating apparatuses 3. Note that the molecular beam generating apparatus 2 is identical to that used in the first embodiment and an explanation thereof is therefore omitted here.

The apparatus of the present embodiment for separating isomers of a chiral substance includes a plurality of the circularly polarized light irradiating apparatuses 3 are provided in each of upper and lower parts of the vacuum chamber 1. Namely, the plurality of the circularly polarized light irradiating apparatuses 3 are horizontally provided in the lower part of the vacuum chamber 1, for emitting circularly polarized light which is identical to that of the first embodiment. On the other hand, a plurality of circularly polarized light irradiating apparatuses 3' are horizontally provided in the upper part of the vacuum chamber 1, for emitting circularly polarized light which is different from that of the first embodiment. Note that (i) each of the plurality of the circularly polarized light irradiating apparatuses 3' and (ii) each of the plurality of the circularly polarized light irradiating apparatuses 3 which are provided in each of the upper and lower parts of the vacuum chamber 1 are alternated. The circularly polarized light irradiating apparatus 3' causes a polarizing device to convert laser light emitted from a semiconductor laser into left-handed circularly polarized light, so that the left-handed circularly polarized light is emitted. This laser light has a frequency causing resonance at an electronic excitation level of the isomer $C_1$ of the chiral substance C. The chiral substance C released by the molecular beam generating apparatus 2 is irradiated with the left-handed circularly polarized light emitted by the circularly polarized light irradiating apparatus 3' from above (see FIG. 2) in a direction which is orthogonal to a direction in which the chiral substance C is in isokinetic linear motion.

A vacuum chamber 1' and the vacuum chamber 1 of the first embodiment are substantially similar to each other, but different in that the vacuum chamber 1' has a lower ceiling than the vacuum chamber 1 of the first embodiment. Isomer inlets 1a and 1b are vertically provided in an upper part of a side wall on the right-hand side of the vacuum chamber 1 (see FIG. 2). Assume that a point of the side wall of the vacuum chamber 1' with which point the chiral substance C released by the molecular beam generating apparatus 2 collides after the isokinetic linear motion (an intersection of a broken line drawn in FIG. 2 and the side wall on the right-hand side) is referred as a collision point. The inlets 1a and 1b are provided so that this collision point is sandwiched therebetween.

When irradiated with no right-handed and left-handed circularly polarized light emitted by the circularly polarized light irradiating apparatuses 3 and 3', respectively, the chiral substance C released by the molecular beam generating apparatus 2 moves rightward in FIG. 2 in isokinetic linear motion in the vacuum chamber 1 and collides with a part of the side wall on the right-hand side of FIG. 2 which part is in the middle of the isomer inlets 1a and 1b which are vertically provided (see an arrow of a one-dot chain line).

The apparatus of the present embodiment for separating isomers of a chiral substance is arranged such that the chiral substance C is irradiated, during the isokinetic linear motion, with (i) the right-handed circularly polarized light emitted from below by the polarized light irradiating apparatus 3 and (ii) the left-handed circularly polarized light emitted from above by of the polarized light irradiating apparatus 3'. This subjects the isomer $C_1$ to (i) a large upward radiation force caused by the right-handed circularly polarized light and (ii) a small downward radiation force caused by the left-handed circularly polarized light. Then, a difference between these radiation forces causes the isomer $C_1$ to have an upward acceleration. In addition, the right-handed circularly polarized light, which has a resonant frequency of the isomer $C_1$, causes the isomer $C_1$ to further increase in upward acceleration. In contrast, the isomer $C_2$ is subjected to (i) a small upward radiation force caused by the right-handed circularly polarized light and (ii) a large downward radiation force caused by the left-handed circularly polarized light. Then, a difference between these radiation forces causes the isomer $C_2$ to have a downward acceleration. In addition, the left-handed circularly polarized light, which has a resonant frequency of the isomer $C_2$, causes the isomer $C_2$ to further increase in downward acceleration. Note that the plurality of the circularly polarized light irradiating apparatuses 3' and the plurality of the circularly polarized light irradiating apparatuses 3 are provided in each of the upper and lower parts of the vacuum chamber 1'. Therefore, the chiral substance C is repeatedly irradiated with the right-handed and left-handed circularly polarized light during the isokinetic linear motion. This causes the isomers $C_1$ and $C_2$ to have their respective severalfold upward and downward accelerations, so that a difference between these accelerations becomes extremely large.

For this reason, the isomer $C_1$ greatly varies in movement direction so as to move upward. Therefore, the isomer $C_1$ is greatly displaced upward as it moves rightward in FIG. 2. As a result, the isomer $C_1$ goes out of the vacuum chamber 1', through the isomer inlet 1a which is provided in the upper part of the side wall of the vacuum chamber 1, to an outside, where the isomer $C_1$ is collected. In contrast, the isomer $C_2$ greatly varies in movement direction so as to move downward. Therefore, the isomer $C_2$ is greatly displaced downward as it moves rightward in FIG. 2. As a result, the isomer $C_2$ goes out of the vacuum chamber 1' through the isomer inlet 1b which is provided in the lower part of the side wall of the vacuum chamber 1. Then, the isomer $C_2$ is collected outside the vacuum chamber 1'.

As a result, according to the apparatus of the present embodiment for separating isomers of a chiral substance, it is possible to separately extract the isomers $C_1$ and $C_2$ from the chiral substance C through the isomer inlets 1a and 1b which are provided in each of the upper and lower parts of the vacuum chamber 1. Furthermore, by the irradiation of the chiral substance C with the right-handed and left-handed circularly polarized light, the directions in which the isomers $C_1$ and $C_2$ are displaced are divided into upward and downward directions, respectively. This eliminates the need of a large-scale vacuum chamber 1. Moreover, the plurality of the circularly polarized light irradiating apparatuses 3 and the plurality of the circularly polarized light irradiating apparatuses 3' irradiate the chiral substance with the circularly polarized light. This allows a difference in displacement amount of the isomers $C_1$ and $C_2$ to be great without increasing respective light intensities of the circularly polarized light irradiating apparatus 3 and the circularly polarized light irradiating apparatus 3'.

Third Embodiment

Figure 3:
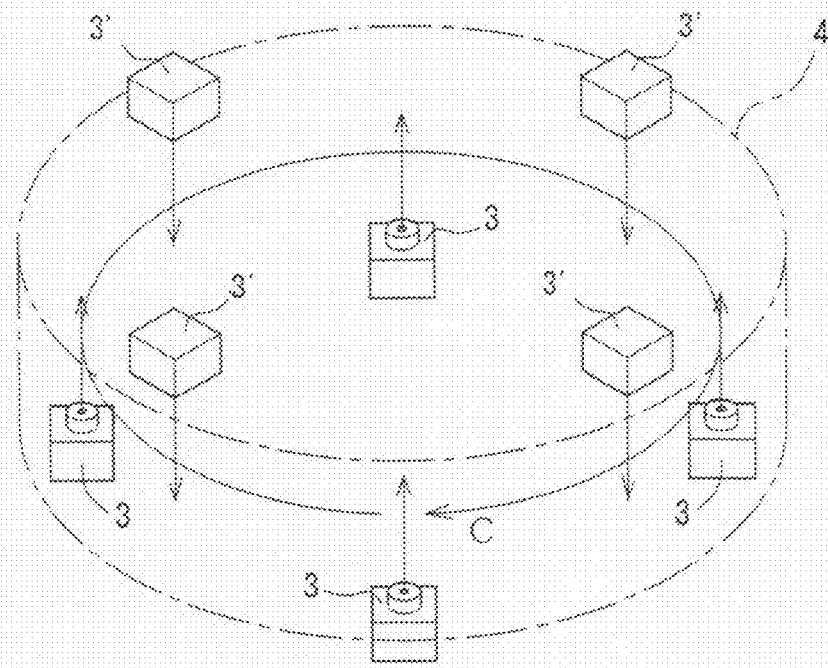
FIG. 3, which shows a third embodiment of the present invention, is a partially-omitted perspective view illustrating an arrangement of an apparatus for separating isomers of a chiral substance.

FIG. 3 illustrates a third embodiment of the apparatus for separating isomers of a chiral substance. A cylindrical container 4 is filled with a fluid medium, and this fluid medium rotates at an equiangular velocity. Note that molecules of a chiral substance identical to those of the first and second embodiments float in and rotates with this fluid medium.

A plurality of circularly polarized light irradiating apparatuses 3' are equiangularly spaced in a rim of a covering plate of the cylindrical container 4, whereas a plurality of circularly polarized light irradiating apparatuses 3 are equiangularly spaced in a rim of a base plate of the cylindrical container 4. Note that (i) each of the plurality of circularly polarized light irradiating apparatuses 3 and (ii) each of the plurality of circularly polarized light irradiating apparatuses 3' are alternated. The circularly polarized light irradiating apparatus 3' provided on the covering plate is identical to the circularly polarized light irradiating apparatus 3' of the second embodiment provided in the upper part of the vacuum chamber 1', whereas the circularly polarized light irradiating apparatus 3 provided on the base plate is identical to the circularly polarized light irradiating apparatus 3 of the second embodiment provided in the lower part of the vacuum chamber 1'.

A chiral substance C which rotates in the cylindrical container 4 is repeatedly irradiated with: (i) right-handed circularly polarized light from below by the circularly polarized light irradiating apparatus 3 provided on the base plate and (ii) left-handed circularly polarized light from above by the circularly polarized light irradiating apparatus 3'. This causes (i) an isomer $C_1$ to have a large upward acceleration and (ii) an isomer $C_2$ to have a large downward acceleration, as is the case with the second embodiment (Note that illustration of the isomers $C_1$ and $C_2$ is omitted in FIG. 3). In addition, the chiral substance C is repeatedly irradiated with the circularly polarized light during the rotation. This causes the isomers $C_1$ and $C_2$ to have their respective larger accelerations, so that a difference between these accelerations becomes extremely large.

For this reason, the isomer $C_1$ is greatly upwardly displaced while rotating, so as to move to the vicinity of the covering plate of the cylindrical container 4. In contrast, the isomer $C_2$ is greatly downwardly displaced while rotating, so as to move to the vicinity of the base plate of the cylindrical container 4.

For this reason, if the fluid medium in the cylindrical container 4 can be vertically separately extracted, it is possible to separate the isomers $C_1$ and $C_2$. Further, provision of the cover and base plates of the cylindrical container 4 with their respective isomer inlets allows a separate extraction of the isomers $C_1$ and $C_2$ with the fluid mediums flown out of these respective isomer inlets.

As a result, according to the apparatus of the present embodiment for separating isomers of a chiral substance, it is possible to separately extract the isomers $C_1$ and $C_2$ from the respective upper and lower fluid mediums provided in the cylindrical container 4.

EXAMPLES

The following describes (i) observations of a principle and (ii) a numerical evaluation of the method for separating isomers of a chiral substance.

Figure 4:
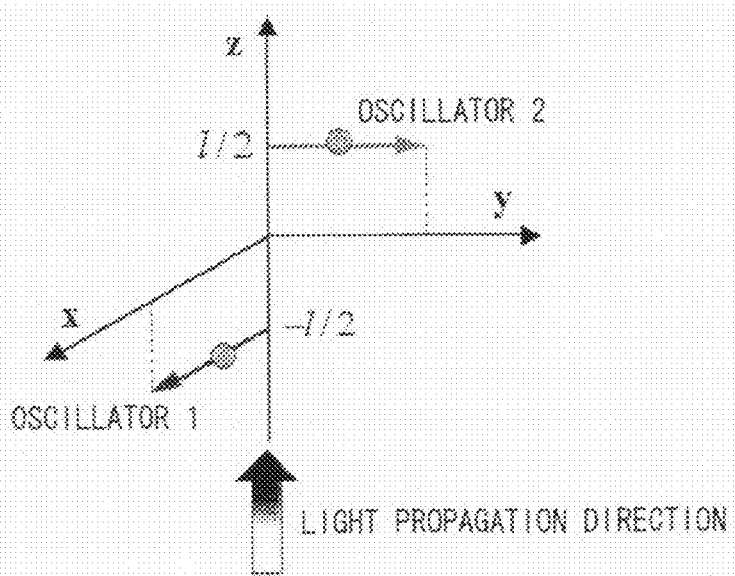
FIG. 4, which shows an example of the present invention, is a diagram illustrating a Coupled-oscillator model.
Figure 5:
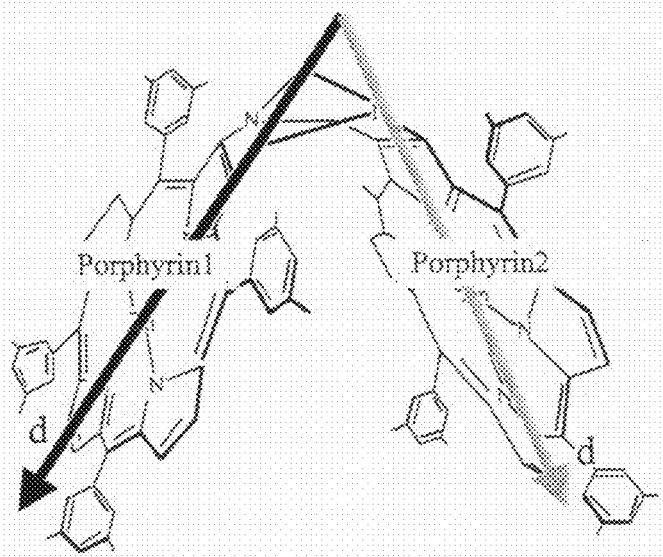
FIG. 5, which shows an example of the present invention, is a drawing illustrating a steric structure of a Troger's base porphyrin dimer.

Each of isomers included in a chiral substance has an optical property such as optical rotatory power and circular dichroism because the isomers have different refractive indices and absorbances with respect to left-handed and right-handed circularly polarized light. Generally, it has been understood that this phenomenon is caused by broken parity symmetry between the isomers due to non-diagonal components of a polarizability tensor of the substance which are included in the respective isomers. It is a Kuhn's Coupled-oscillator model that theoretically explains, by a classical approach, a mechanism in which this broken parity symmetry occurs. This theory assumes two punctuate oscillators (oscillators 1 and 2) which are arranged as illustrated in FIG. 4 and oscillate in directions of respective arrows so as to interact with each other. The Coupled-oscillator model regards a bond system of two oscillators as a chiral molecule obtained by bonding two monomers with each other, and finds a relational expression (see the following mathematical expression (1)) between an induced polarization P and an incident electric field $E^b$ so as to show that a polarizability tensor has non-diagonal components.

[Math. 1]

$$P = \frac{e^2 f_0}{(k_1 - m\omega^2)^2 - k_2^2} \begin{bmatrix} k_1 - m\omega^2 & -k_2\exp(-iql) \\ -k_2\exp(iql) & k_1 - m\omega^2 \end{bmatrix} E^b \quad (1)$$

$k_1$: Self-interaction coefficient
$k_2$: Inter-oscillator interaction coefficient
e: Oscillator electric charge
$f_0$: Oscillator strength
m: Oscillator mass
q: Light wave number The mathematical expression (1) shows that (i) an expression of the polarization P varies when a different beam of circularly polarized light is emitted as $E^b$ and (ii) isomers of the chiral molecule assumed in FIG. 4 which isomers are obtained in a case where a z-x plane is a mirror image plane are differently polarized even if the chiral molecule is irradiated with an identical beam of circularly polarized light. In view of this, the present inventors conceived an idea such that employment of the foregoing principle of resonant light manipulation leads to (i) a new-type optical manipulation by a resonant radiation force in which a quantum mechanical property of a chiral minute object is reflected by use of light which has an angular momentum and (ii) an isomer separation which can attain the foregoing object. In research carried out by a group of the present inventors, research and invention have been made concerning selection and manipulation of a nanosubstance which are carried out by a resonant radiation force in which a quantum mechanical property depending on a difference in size, form, internal structure, and the like of a given nanosubstance is utilized. However, this research was mainly based on theoretical research in which a nanosubstance excellent in symmetry is subjected to manipulation. Therefore, a discussion on an asymmetric geometrically-structured nanosubstance such as a chiral substance remained as a future problem to be solved.

Patent Literature 3 discloses a technique which focuses on circularly polarized light. However, this technique, which is merely employed for providing achiral source of a method for chemical asymmetric synthesis, does not consider separating a chiral substance by mechanical motion control in a photo-excited state. Further, Patent Literature 3 makes no disclosure that a chiral nanosubstance is mechanically manipulable by exerting a radiation force thereon by circularly polarized light irradiation. In view of the circumstances, on the basis of a microscopic nonlocal response theory and an equation of Lorentz force, the present inventors diligently studied on how much a radiation force caused in a case where a chiral minute object is irradiated with resonant light such as circularly polarized light which has an angular momentum is dependent upon kinds of polarization and chirality and upon photon energy. As a result of the diligent study, the present inventors finally accomplished the present invention.

The following briefly explains a method for calculating an induced polarization and a response electric field which are necessary in evaluating, by the microscopic nonlocal response theory, a resonant radiation force exerted on a chiral molecule. First, the induced polarization which is necessary for evaluation of the resonant radiation force is determined as the following mathematical expressions (2) by self-consistently solving a Maxwell equation whose source is the induced polarization P which is derived from a Schrodinger equation which includes Hamiltonian whose perturbation term is an interaction including a retardation effect between polarization and an electric field.

[Math. 2]

$$\begin{aligned} P(r, \omega) &= \sum_i X_i \vec{\rho}_i(r)^* \\ SX &= X^b \\ S &= [(E_i - \hbar\omega - i\gamma)\delta_{ij} + A_{ij}] \\ X &= [X_i]^T \\ X^b &= [X_i^b]^T \\ X_i^b &= \int_v dr \vec{\rho}_i(r) \cdot E^b(r, \omega) \end{aligned} \quad (2)$$

where a suffix i is a number of a site, $X_i$ is a complex amplitude of a polarization, and the following mathematical expression (3) is a transition dipole density.

[Math. 3]

$$\vec{\rho}_i(r) = \rho_i(r)\vec{\xi} \quad (3)$$

where $p_i(r)$ is an amplitude of the transition dipole density, and the following vector (4) included in the mathematical expression (3) is a unit vector indicating a direction.

[Math. 4]

$$\vec{\xi} \qquad (4)$$

S is a coefficient matrix of simultaneous equations for determining X, E is eigenenergy of the ith site, the following energy (5) included in the mathematical expressions (2) is energy (a frequency) of incident light, $\gamma$ is a nonradiative width, $\delta_{ij}$ is Kronecker delta, $A_{ij}$ is a dipole interaction via an electromagnetic field, X is a longitudinal vector of $X_i$ in which i is a row number, and $X^b$ is a longitudinal vector of $X_i^b$ of an interaction $X_i^b$ between an induced polarization and an incident field in which interaction $X_i^b$ i is a row number.

[Math. 5]

$$\hbar\omega$$

As an example of application of the present theory, the simultaneous equations with respect to X which are included in the mathematical expressions (2) are solved on the assumption that there are two finite-sized dipoles which are orthogonal to each other and whose transition dipoles are arranged similarly to those illustrated in FIG. 4 so as to be equal in size. Then, the induced polarization P which corresponds to the mathematical expression (1) is given to the following mathematical expression (6).

[Math. 6]

$$P(r, \omega) = \frac{\rho_i(r)}{(\overline{E}_i - \hbar\omega - i\overline{\Gamma}_i)^2 - A_{ij}A_{ji}} \begin{bmatrix} \overline{E}_i - \hbar\omega - i\overline{\Gamma}_i & -A_{ij} \\ -A_{ij} & \overline{E}_i - \hbar\omega - i\overline{\Gamma}_i \end{bmatrix} X^b \qquad (6)$$

Note here that the following mathematical expression (7) expresses eigenenergy of the ith site which eigenenergy includes self-interaction and

[Math. 7]

$$\overline{E}_i = E_i + Re[A_{ii}] \qquad (7)$$

the following mathematical expression (8) expresses a sum of a nonradiative width and a radiative width.

[Math. 8]

$$\overline{\Gamma}_i = \gamma - Im[A_{ii}] \qquad (8)$$

In comparison between the mathematical expressions (1) and (6), the mathematical expression (1) explains a mechanism of chirality on the basis of a phenomenalistic physical quantity such as an oscillator strength and a self-interaction coefficient, whereas the respective quantities expressed in the mathematical expression (6) are self-consistently determined by the Schrodinger equation and the Maxwell equation. This clearly attaches a microscopic meaning to the mechanism of chirality. Further, in the mathematical expression (1), each of the oscillators is approximately regarded as a point dipole. In contrast, the mathematical expression (6) is applicable to a chiral molecule or a nanostructure which has any size and form, and can also include quantum mechanical information of a substance. It is therefore possible to say that the present theory is a more general expression as compared to the case of the mathematical expression (1). In addition, the mathematical expression (6) shows that $A_{ij}$ is important in determining chirality and has a quantity in which information on (i) a geometric structure of a monomer constituting a chiral molecule and (ii) a spatial structure of an electromagnetic field is reflected.

In a case where after a model, irrespective of the model illustrated in FIG. 4, of an object chiral molecule is given, the induced polarization P obtained by the mathematical expressions (2) and a response electric field expressed in the following mathematical expression (9):

[Math. 9]

$$E(r,\omega) = E^b(r,\omega) + \int_V dr' G^b(r,r',\omega) \cdot P(r',\omega) \qquad (9)$$

E: Response electric field
G: Green function are substituted for the following mathematical expression (10) which is an analytical expression of a radiation force derived from the Lorentz equation,

[Math. 10]

$$\langle F(\omega) \rangle = \frac{1}{2} Re\left[ \int_v dr (\nabla E(r, \omega)^*) \cdot P(r, \omega) \right] \qquad (10)$$

it is possible to numerically evaluate a resonant radiation force in which a microscopic spatial structure of an object substance is reflected.

The following assumes, as a specific calculation model, a case where a Troger's base porphyrin dimer in which two porphyrins represented by dipoles are bonded in a chiral arrangement (see FIG. 5) is irradiated with plane-wave circularly polarized light. A radiation force obtained in the case is evaluated by use of the mathematical expressions (2), (9), and 10).

A porphyrin assembly system including the porphyrin dimer used here is one of the main object substances for research in complex chemistry and supermolecular chemistry. The porphyrin assembly system becomes a pigment which causes light absorption and light emission in a ultraviolet-visible region. For this reason, the porphyrin assembly system is a versatile organic substance which is expected to be applied to various fields such as a solar cell and an organic EL light emitting device. In addition, there have been numerous reports on a porphyrin assembly system which has a geometrical structure in which chirality occurs. The porphyrin dimer studied in the reports is one of the specific examples of such a geometrically-structured porphyrin integrated. The Troger's base porphyrin dimer was used particularly because: (i) details of transition dipole moment obtained in a molecule are clear and the transition dipole moment has a simple form which is close to that of the Kuhn's Coupled-oscillator model, and (ii) a UV-vis. spectrum and a spectrum of circular dichroism are clear (see Reference 2, for example) and an optical property and a radiation force can be clearly associated with each other. In particular, it has been confirmed that a difference in radiation force between enantiomers which difference is caused when the enantiomers are irradiated with left-handed or right-handed circularly polarized light is proportional to the spectrum of circular dichroism.

Figure 6:
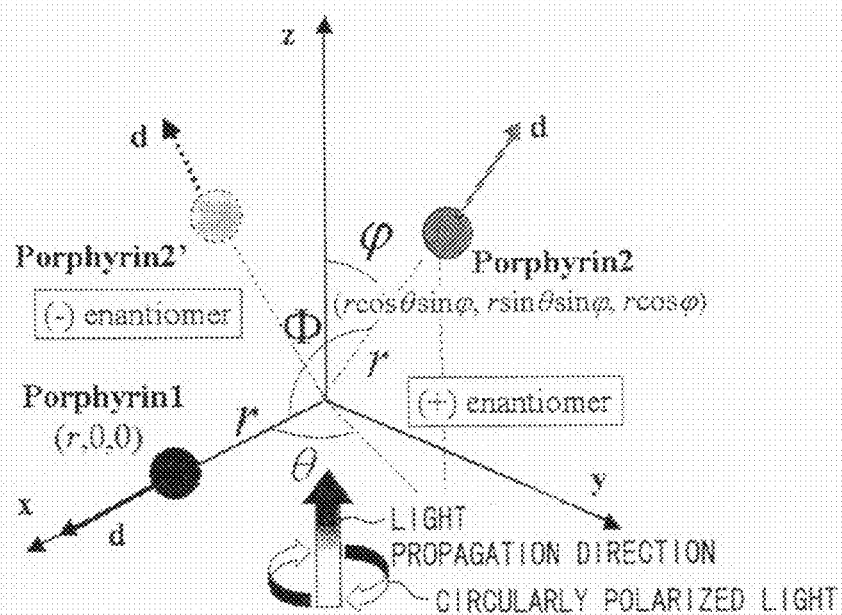
FIG. 6, which shows an example of the present invention, is a diagram illustrating a modeled porphyrin dimer.

Two porphyrins are equally distant from a Troger's base bond part located at the origin (see FIG. 6). Electric dipole moment obtained on an axis which connects the bond part to a nitrogen atom is expressed in the following mathematical expression (11). (Actually, though transition dipoles occur also in a direction which is orthogonal to the axis, the transition dipoles seem to be slightly different in resonant wavelength from the electric dipoles. The transition dipoles are ignored here so that a calculation model is simplified.)

[Math. 11]

$$d = \int_r dr\, \vec{\rho}_i(r) \quad (11)$$

Assume that (i) an x-y plane is a mirror image plane and (ii) (a) a pair of a porphyrin 1 and a porphyrin 2 and (b) a pair of the porphyrin 1 and a porphyrin 2' are a (+) enantiomer and a (−) enantiomer, respectively.

Figure 7A:
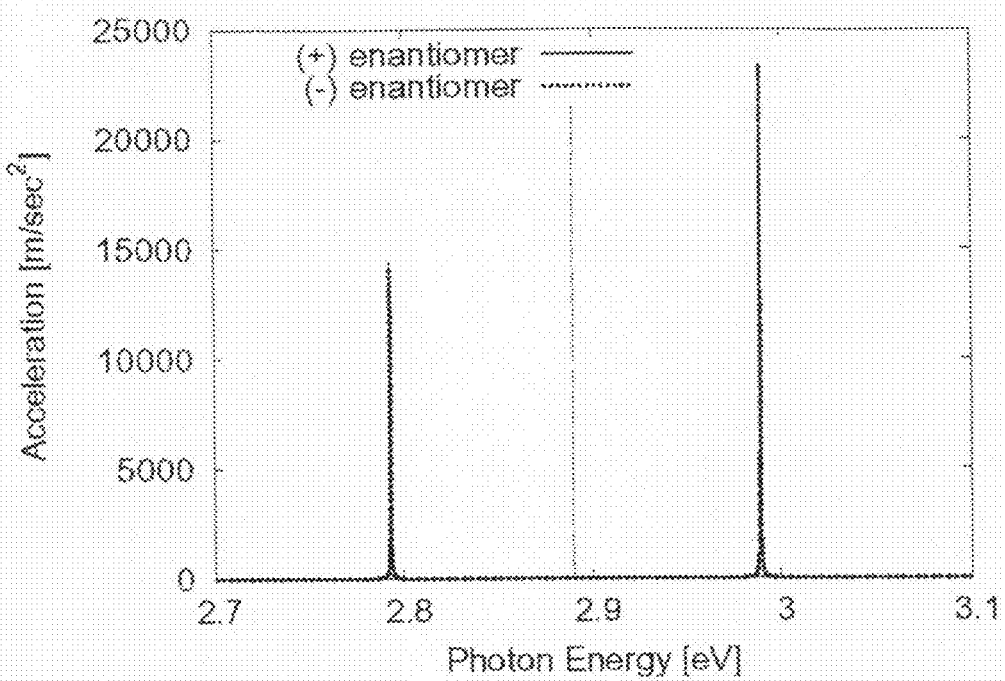
FIG. 7($a$), which shows an example of the present invention, is a graph illustrating photon energy dependences (in a z-axis direction) of accelerations applied to respective enantiomers in a case where a porphyrin dimer is used.
Figure 7B:
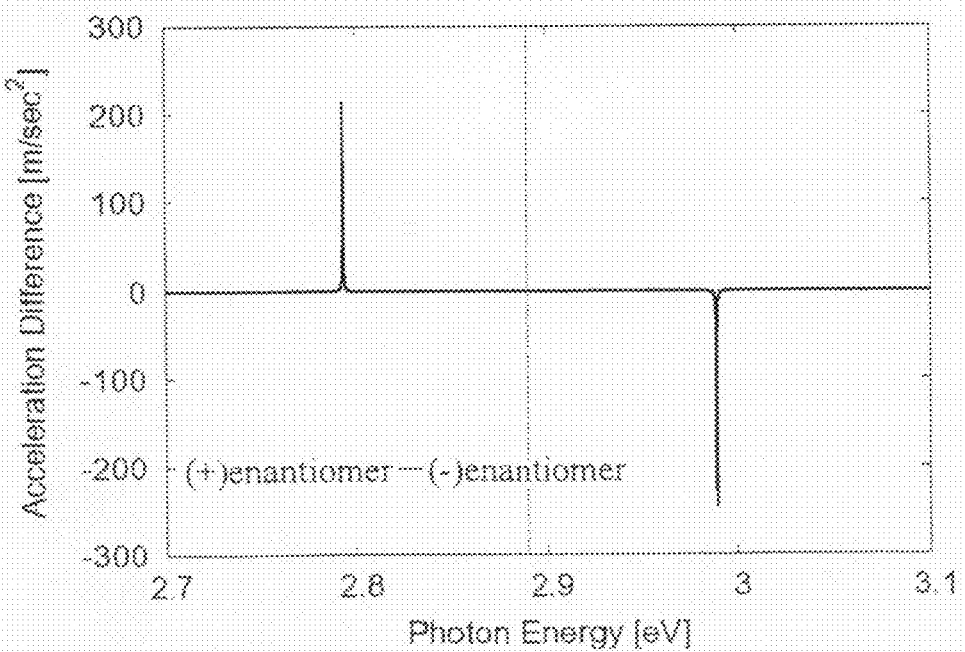

First, radiation forces exerted on the respective molecules ((+) enantiomer and (−) enantiomer) were examined when the respective molecules were irradiated with circularly polarized light propagated in a z-axis direction (i.e., a direction illustrated in FIG. 6). FIGS. 7(*a*) and 7(*b*) show results of the examination. FIG. 7(*a*) is a graph illustrating photon energy dependences of accelerations applied to the respective enantiomers (in the z-axis direction). FIG. 7(*b*) is a graph illustrating a difference in acceleration applied to the respective enantiomers (in the z-axis direction). Note that parameters of the molecule which were used here are: $\Phi=81°$, $\varnothing=45°$, porphyrin center distance=8.38 [Å], electric dipole moment $|d|=8.06$ [Debye], simplicial excitation energy including self-interaction=2.89 [eV], and mass of porphyrin dimer per molecule=$2.66 \times 10^{-24}$ [kg]. Note also that a cryogenic condition obtained in superfluid helium (see an experiment disclosed in Reference 1) was assumed and the sum Γi of a nonradiative width and a radiative width was set to 0.2 [meV]. An intensity of incident light was assumed to be 8.44 [W/cm$^2$] which is an order identical to that used in laser cooling of an atom. A radiation force is proportional to an intensity of incident light in a linear response region. FIG. 7(*b*) illustrates a difference in acceleration which difference is caused by radiation forces applied to the respective enantiomers. According to FIG. 7(*a*), there seems to be hardly any difference in radiation force applied to the respective enantiomers. However, FIG. 7(*b*) shows that there is a difference in acceleration which difference is approximately two digit larger than a gravitational acceleration under the assumed condition in the vicinities of resonance energy which is split into two by a dipole interaction occurring in a monomer constituting a dimer. This result shows that it is possible to realize an isomer separation if a distance for which isomers are displaced can be increased by such a simple manipulation of continuously irradiating an isomeric mixture (a chiral substance) with circularly polarized light which rotates in a given direction.

Figure 8A:
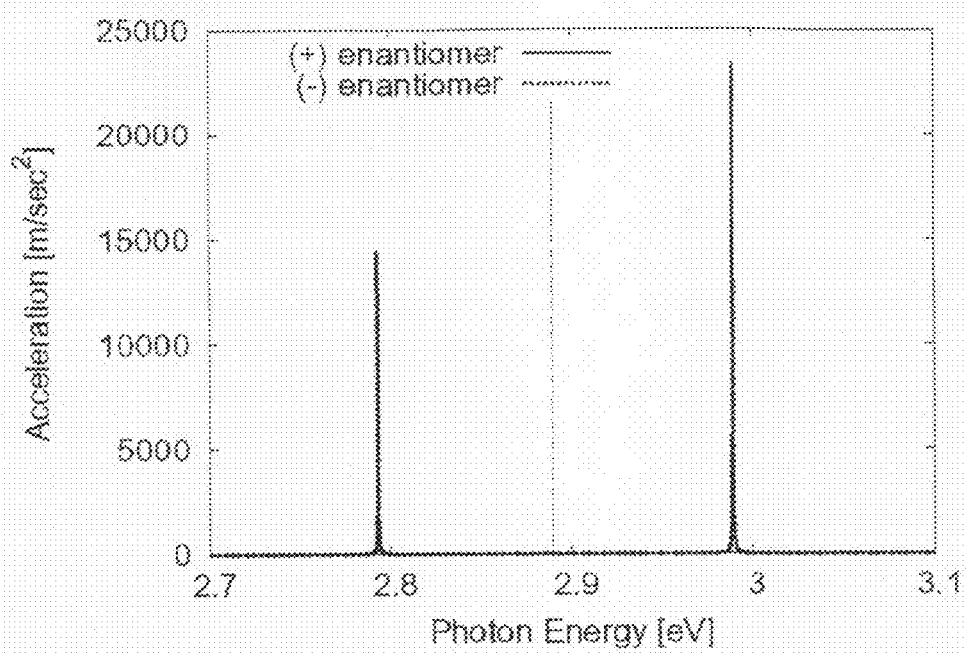
FIG. 8($a$), which shows an example of the present invention, is a graph illustrating photon energy dependences (in a z-axis direction) of accelerations applied to respective enantiomers in a case where incident circularly polarized light rotates in an opposite direction to that illustrated in FIG. 6.
Figure 8B:
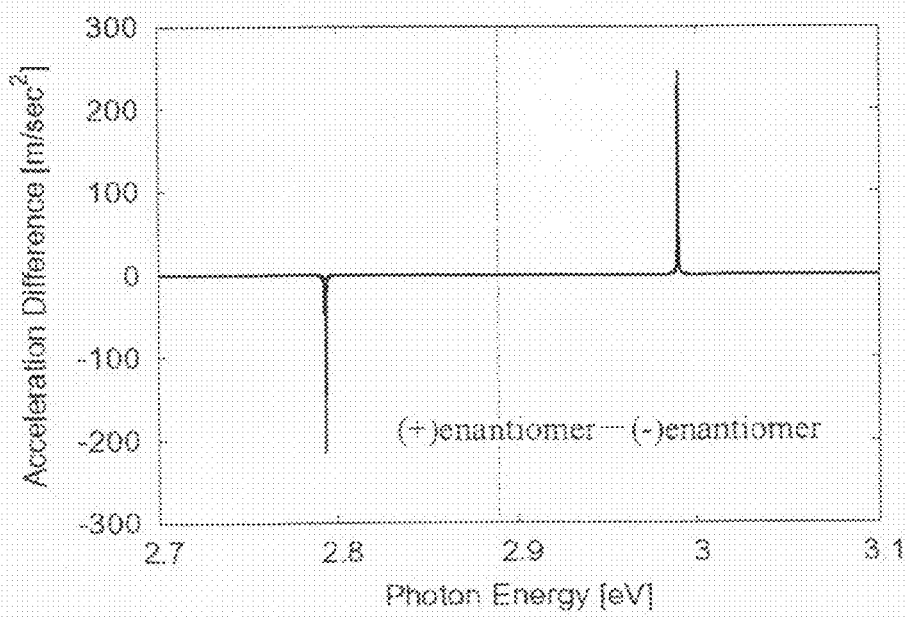
Figure 10A:
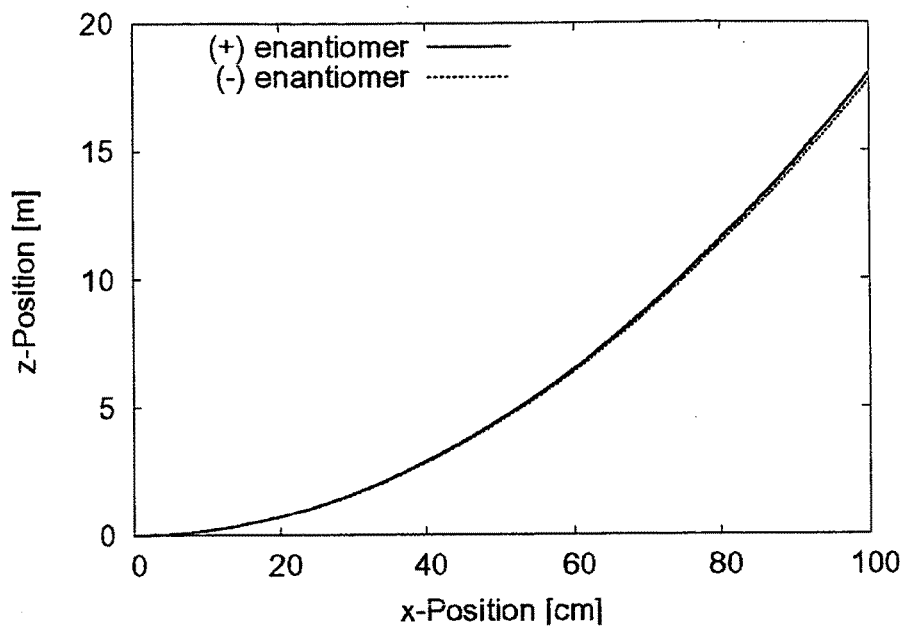
FIG. 10($a$), which shows an example of the present invention, is a graph illustrating distances flown by respective enantiomers in x-axis and z-axis directions, which distance is numerically calculated under a laboratory model for an enantiomer separation (250-time emission of circularly polarized light at regular intervals for a flight distance of 1 m, spot size of laser: 1 mm, initial velocity of molecular beam: 10 m/s).
Figure 10B:
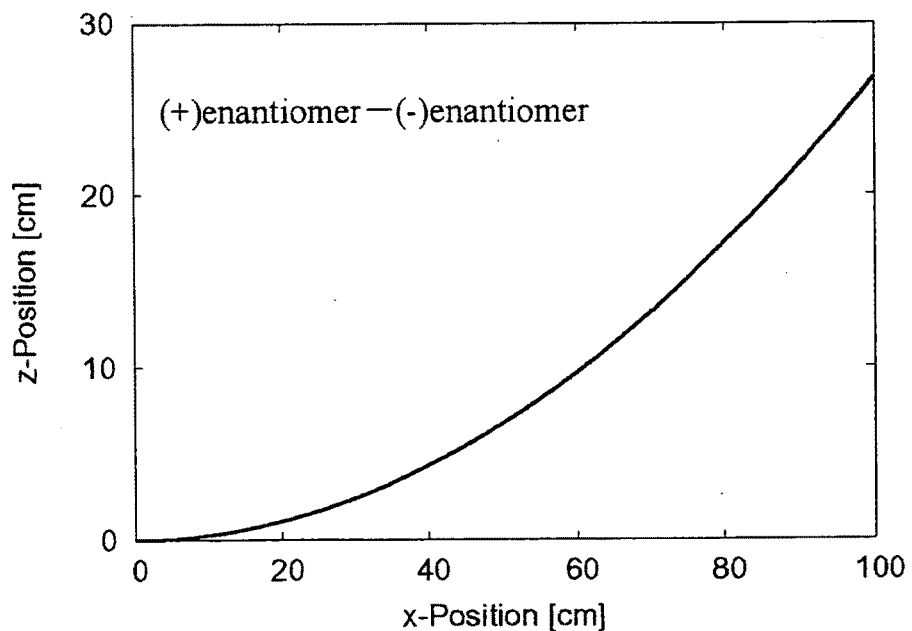

Next, radiation forces exerted on the respective molecules ((+) enantiomer and (−) enantiomer) were examined when the respective molecules are irradiated with circularly polarized light which rotates in an opposite direction to the circularly polarized light illustrated in FIG. 6. FIGS. 8(*a*) and 8(*b*) show calculation results of the examination. FIG. 8(*a*) is a graph illustrating photon energy dependences of accelerations applied to the respective enantiomers (in a z-axis direction). FIG. 8(*b*) is a graph illustrating a difference in acceleration applied to the respective enantiomers (in the z-axis direction). FIG. 8(*a*) has a spectrum which is substantially identical to that of FIG. 7(*a*), whereas FIG. 8(*b*) has a spectrum structure such that the difference in acceleration is opposite in sign to that of FIG. 7(*a*). This shows that there exist differences between (i) resonance positions of the respective enantiomers and (ii) left-handed and right-handed circularly polarized light depending on how the enantiomers and the left-handed and right-handed circularly polarized light are combined. The following exemplifies a technique of an enantiomer separation which technique employs this principle. FIG. 9 exemplifies a technique of the enantiomer separation which technique employs the calculation results illustrated in FIGS. 7(*a*) and 7(*b*) and FIGS. 8(*a*) and 8(*b*). In the technique of the enantiomer separation (see FIG. 9), a molecular beam of an enantiomeric mixture is emitted in an x-axis direction and irradiated several times with circularly polarized light which rotates in a given direction, from a z-axis direction which is perpendicular to the x-axis direction. In a case where the enantiomeric mixture is irradiated with the circularly polarized light during the emission of the molecular beam, an affinity between a direction in which the circularly polarized light rotates and a chiral molecule causes a difference, in the z-axis direction, in acceleration between the (+) enantiomer and the (−) enantiomer. Finally, the enantiomers reached their respective given destinations so as to be separate from each other in the z-axis direction. FIGS. 10(*a*) and 10(*b*) illustrate results in each of which such an enantiomer separation is actually numerically calculated. FIG. 10(*a*) is a graph illustrating a calculation result of a difference in distance flown by the respective enantiomers in the x-axis and z-axis. FIG. 10(*b*) is a graph illustrating a calculation result of a difference in flight distance in distance flown by the respective enantiomers in the x-axis and z-axis. The results illustrated in FIGS. 10(*a*) and 10(*b*) show that there is finally a macro distance between the molecules as compared to their respective sizes. Note, however, that the molecules may fly excessively in the z-axis direction. For this reason, it is possible to build an experimental system in which only a difference in radiation force exerted on the respective molecules can be utilized, by irradiating (i) from the z-axis, the respective molecules with circularly polarized light which rotates in a given direction (see the model illustrated in FIG. 9) and (ii) from a −z-axis direction, circularly polarized light which rotates in an opposite direction to the circularly polarized light which rotates in the given direction. Further, it is also possible to cause a macro difference on a path of an isomeric mixture by preparing a flow path also in a fluid medium, causing the isomeric mixture to be on a flow for a long distance, and irradiating, as illustrated in FIG. 3, the isomeric mixture more than once with circularly polarized light from a direction which is orthogonal to a direction in which the isomeric mixture flows. This allows an isomer separation.

An object substance in these calculation results, each being based on the Coupled-oscillator model, is not limited to a porphyrin dimer. The calculation results generally disclose that a chiral substance in which a difference in absorption of left-handed and right-handed circularly polarized light (this is referred to as circular dichroism) is seen causes a difference in radiation force. Therefore, the calculation results are versatilely applicable.

For example, it is possible to employ the present invention for a carbon nanotube because the carbon nanotube, whose enantiomers are different in absorption of left-handed and right-handed circularly polarized light, also shows circular dichroism (see Reference 3).

Figure 11:
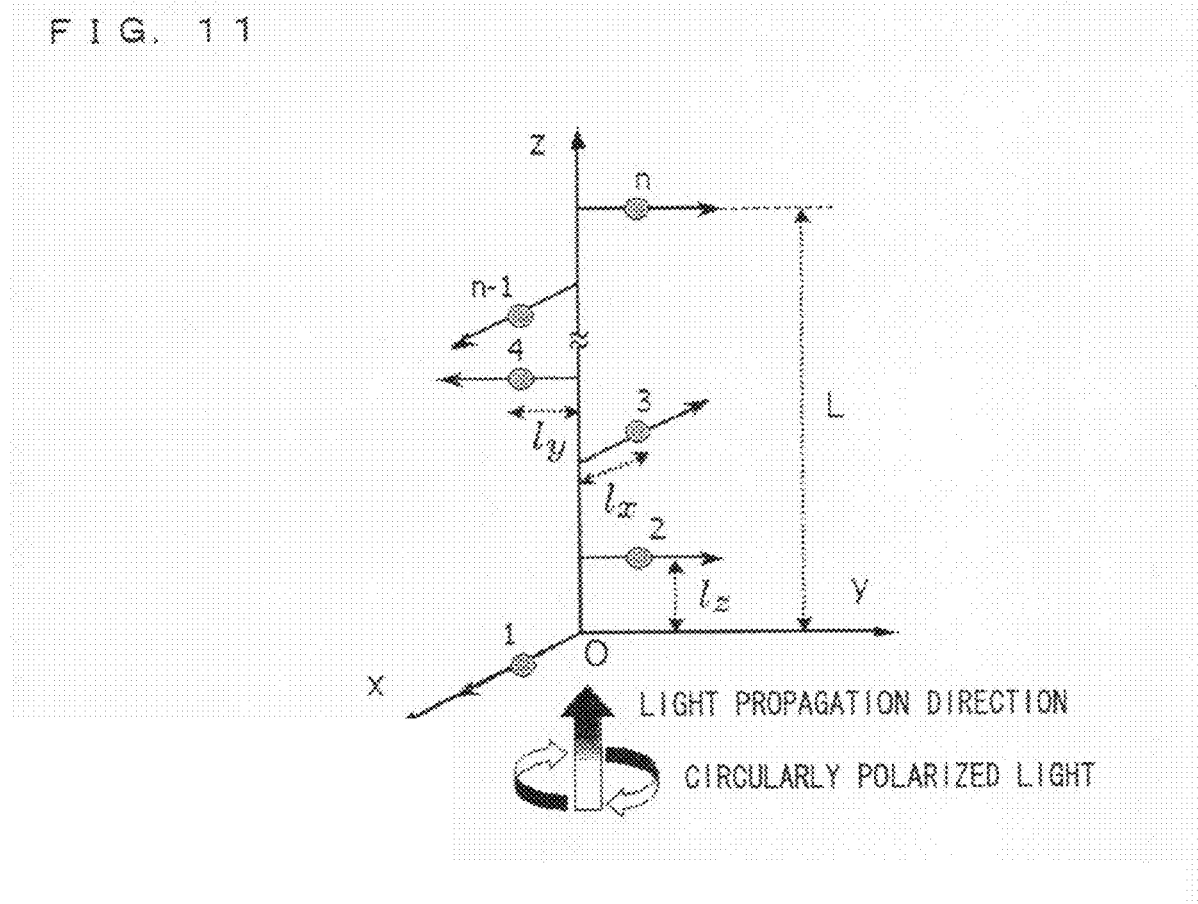
FIG. 11, which shows an example of the present invention, is a diagram illustrating a model for an arrangement of dipoles of a helical minute object.

Next, a minute object is to be considered in which n dipoles (atoms/molecules) are helically arranged at a rotation angle θ with respect to a z-axis (see FIG. 11). Such a helical minute object is not particularly limited and is exemplified by a nucleic acid such as DNA and a helically-structured porphyrin polymer (see Reference 4). FIG. 11 illustrates helically arranged dipoles whose rotation angle is θ=90°. (i) A minute object which has such an arrangement (a helix which is right-handed seen from a direction of incident light) and (ii) an isomer of the minute object whose mirror image plane is an x-z plane (a helix which is left-handed seen from the direction of incident light) are regarded as (+) enantiomer and (−) enantiomer, respectively. In the arrangement of the dipoles (see FIG. 11), a rotation by 360 degrees is realized by four dipoles, and a set of four dipoles is therefore referred to as one revolution. FIG. 12 is an evaluation carried out with respect to such a model under a cryogenic condition similar to that described above. In the evaluation, resonant radiation forces are numerically calculated which are caused when the enantiomers are irradiated from a z-axis direction with plane-wave circularly polarized light which rotates in a direction illustrated in FIG. 11. Note that parameters of a single dipole which parameters are used here are: electric dipole moment |d|=8 [Debye], excitation energy including self-interaction=2.89 [eV], and mass=1.33×10$^{-24}$ [kg] on the assumption that the dipole is a Zn-porphyrin transition dipole. Note also that a parameter of the minute object illustrated in FIG. 11 which parameter is used here is: $1_x=1_y=4$ [Å], $1_z=1$ [nm]. The evaluation was carried out by a calculation method such that a response field obtained in the case of n dipoles was determined by the mathematical expressions (2) and thereafter substituted for the mathematical expression (10). FIG. 12(a) shows that though peak values of accelerations applied to the entire minute object are substantially equal when the number of revolutions increases, a resonant frequency of the minute object sensitively varies in position. This result shows that it is possible to apply an effective radiation force only to a minute object which has a given size and number of revolutions by adjusting a frequency of incident light and to select a size and the number of revolutions of a minute object. On the other hand, peak values of differences in acceleration increase in proportion to the number of revolutions (see FIG. 12(b)). This result shows that a nanocrystallized or polymerized chiral molecule causes a larger difference in resonant radiation force of chirality which difference is caused by circularly polarized light than a simple chiral molecule. Normally, when an isomeric mixture of a chiral molecule is crystallized, it becomes any one of three types: (i) a racemic compound (in which enantiomers are paired and crystallized), (ii) a racemic solid solution (in which both enantiomers are randomly sequenced and crystallized), and (iii) a racemic mixture (a mixture of enantiomers which are separately crystallized). In this case, the nanocrystallized chiral molecule refers to a nanocrystal of a racemic mixture. Reference 5 reports that, by use of an additive, caused asparagine (a kind of an amino acid) to undergo crystal growth as a racemic mixture, instead of crystal growth as a racemic compound as asparagine usually does. Separation by nanocrystallization can be more extensively applied in combination with such a method. Further, a chiral crystal constituted by an achiral molecule is also applicable. Therefore, the results of FIGS. 12(a) and 12(b) show that irradiation of a nanocrystal or a polymer which has chirality with circularly polarized light also allows an effective isomer separation. Concurrently, it is possible to select a size and the number of revolutions of a minute object.

On the other hand, it is also possible to practically apply the separation by nanocrystallization to a measuring technique of the distribution of circular dichroism, a polymerization degree, a size, and the like of a separated isomer and to an analysis of a polarization structure of a chiral substance by detecting the presence and a spatial position of the separated isomer on the basis of these principles.

Figure 13A:
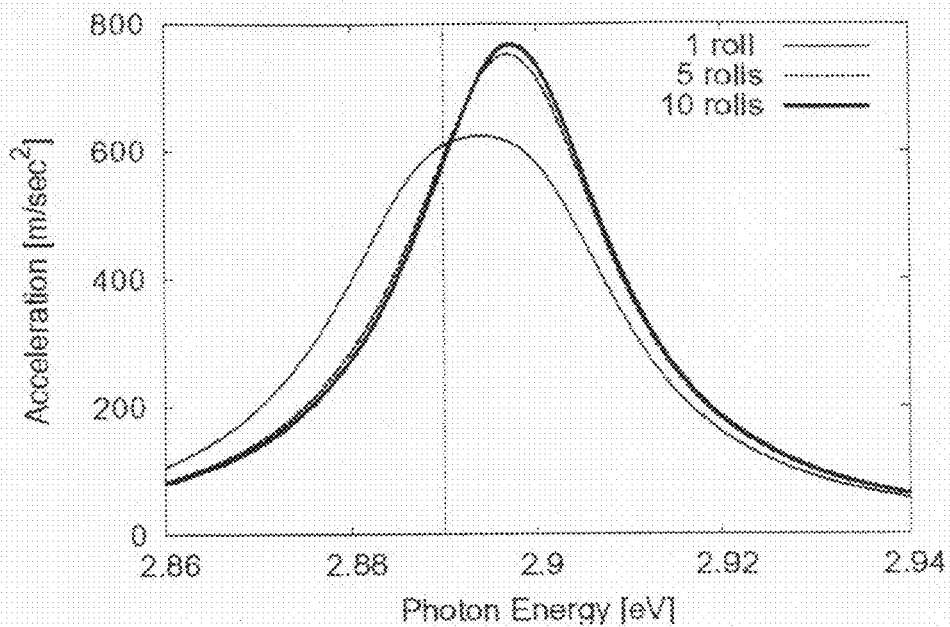
FIG. 13(a), which shows an example of the present invention, is a graph illustrating a photon energy dependence of an acceleration applied to a (+) enantiomer, which photon energy dependence is calculated under the model for the arrangement of the dipoles of the helical minute object (number of revolutions: 1, 5, and 10), assuming approximately room temperature condition.
Figure 13B:
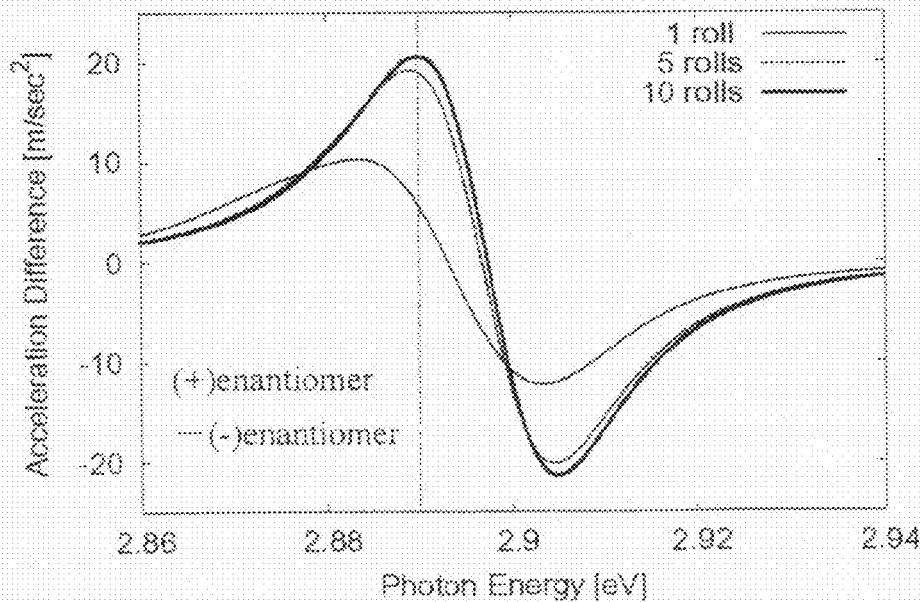
FIG. 13(b), which shows the example of the present invention, is a graph illustrating a difference in acceleration applied to the (+) enantiomer and a (−) enantiomer, which difference is calculated under the model for the arrangement of the dipoles of the helical minute object (number of revolutions: 1, 5, and 10), assuming approximately room temperature condition.
Figure 14:
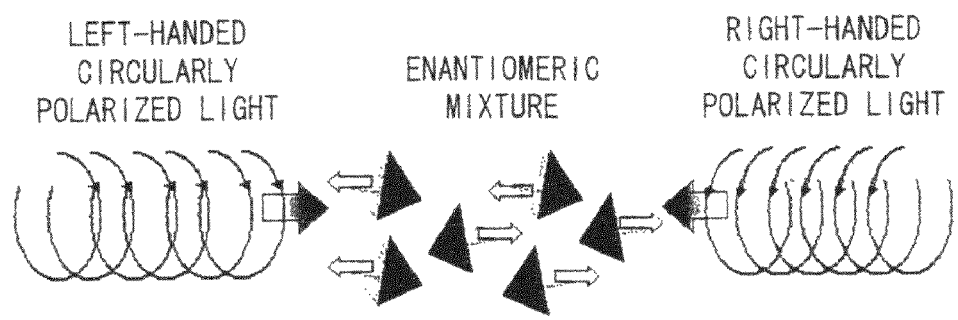
FIG. 14, which shows an example of the present invention and is an alternative example of the principle of the apparatus for separating enantiomers, is a schematic view illustrating a case in which enantiomers are separated by solely utilizing a difference in radiation force applied to the respective enantiomers in such a manner that: an enantiomeric mixture is irradiated, from both sides thereof, with beams of polarized light which rotate in different directions.

Finally, calculation was carried out similarly to the case of FIG. 12. In the calculation, assumed is a sum of a nonradiative width and a radiative width which sum is substantially equivalent to thermal energy at room temperature (when doubled, Γi=12.5 meV, which is half width at half maximum, becomes a value which can be compared with thermal energy at room temperature.) FIG. 13 shows a result of the calculation. There was a fear of not effectively obtaining a difference in acceleration applied to the respective enantiomers because a weaker resonance effect is obtained at room temperature than under a cryogenic condition. However, FIG. 13(b) shows that a difference in acceleration applied to the respective enantiomers and a total ratio between the accelerations do not depend so much on the sum of a nonradiative width and a radiative width and have orders which are approximately one-several tenth of the accelerations. This case also shows that an increase in number of revolutions of the helix tends to cause a larger difference in acceleration. In calculation employing a given laser strength, an acceleration decreases as the sum of a nonradiative width and a radiative width increases. However, an increase in strength of laser light causes an increase in acceleration and also allows a larger difference in acceleration. For example, optical tweezers employ intense incident light whose level is equivalent to MW/cm$^2$ ($10^6$ W/cm$^2$) by focusing laser light (see Reference 6). Use of such a light source causes a larger difference in acceleration also in a fluid at room temperature, so that an enantiomer separation is realized. Further, it is also possible to separate enantiomers by effectively utilizing a difference in acceleration applied to the respective enantiomers in such a manner that an isomeric mixture is sandwiched between two beams of circularly polarized light with which the isomeric mixture is irradiated from opposite directions and which rotate in opposite directions.

REFERENCES

Reference 1: K. Inaba, K. Imaizumi, K. Katayama, M. Ichimiya, M. Ashida, T. Iida, H. Ishihara and T. Itoh, physica status solidi (b) Vol. 243 pp. 3829-3833 (2006)

Reference 2: T. Mori, T. Yamamura, J. Comput. Chem. Jpn., Vol. 4, No. 3, pp. 107-118 (2005).

Reference 3: A. Sanchez-Castillo, C. E. Roman-Velazquez and Cecilia Noguez, Physical Review B Vol. 73, 045401 (1-7) (2006).

Reference 4: S. Geremia, L. Di Costanzo, G. Nardin, L. Randaccio, R. Purrello, D. Sciotto, R. Lauceri, F. Pichierri, Inorg. Chem., Vol. 43, pp. 7579-7581, (2004).

Reference 5: N. Doki, M. Yokota, S. Sasaki and N. Kubota, Cryst. Growth & Des. Vol. 4 pp. 1359-1363 (2004).

Reference 6: S. Ito, H. Yoshikawa, and H. Masuhara, Appl. Phys. Lett. Vol. 80, pp. 482-484 (2002).

Note that all the academic literatures and patent literatures cited in the present specification are quoted as references in the present specification.

As described earlier, an isomer separation method for a chiral substance of the present invention, includes: irradiating the chiral substance which is a mixture of different isomers, with circularly polarized light or elliptically polarized light, so as to cause a difference in acceleration between the different isomers; and separating the different isomers in accordance with the difference in acceleration.

Further, as described earlier, an isomer separation apparatus for a chiral substance of the present invention, includes: circularly polarized light irradiating means for irradiating the chiral substance which is a mixture of different isomers, with circularly polarized light or elliptically polarized light; and isomer separating means for separating at least one of the different isomers from the chiral substance in accordance with a difference in acceleration between the different isomers of the chiral substance.

This realizes a method and an apparatus, each of which requires no contact treatment and no chemical reaction, for separating isomers of a chiral substance.

The isomer separation method of the present invention is preferably arranged such that the chiral substance exists under vacuum or in a fluid medium containing a gas.

The isomer separation method of the present invention is preferably arranged such that the circularly polarized light or elliptically polarized light has a frequency causing resonance at an electronic excitation level of any one of the different isomers included in the chiral substance.

Irradiation of a chiral substance with such circularly polarized light or elliptically polarized light causes a larger difference in radiation force between isomers. This thus allows a more accurate isomer separation.

The isomer separation method of the present invention is preferably arranged such that: the chiral substance is irradiated with two beams of the circularly polarized light or elliptically polarized light which rotate in different directions; and one and the other of the two beams are emitted from (i) a given direction and (ii) a direction different from the given direction, respectively.

This allows a larger difference in acceleration between the isomers.

The isomer separation apparatus of the present invention is preferably arranged such that the light emitted by the circularly polarized light irradiating means has a frequency causing resonance at an electronic excitation level of any one of the different isomers included in the chiral substance.

This causes a larger difference in radiation force between the isomers. This thus allows a more accurate isomer separation.

The isomer separation apparatus of the present invention is preferably arranged such that: the circularly polarized light irradiating means irradiates the chiral substance with two beams of the circularly polarized light or elliptically polarized light which rotate in different directions; and one and the other of the two beams are emitted from (i) a given direction and (ii) a direction different from the given direction, respectively.

This allows a larger difference in acceleration between the isomers.

It is preferable that the isomer separation apparatus of the present invention further include: chiral substance releasing means for unidirectionally releasing the chiral substance into the medium, the circularly polarized light irradiating means emitting the light from a direction which intersects with the direction into which the chiral substance is released.

This allows a larger difference in acceleration between the isomers.

It is preferable that the isomer separation apparatus of the present invention further include: medium rotating means for rotating the fluid medium containing the chiral substance, the circularly polarized light irradiating means emitting the light from a direction which intersects with a radius vector rotation plane of the rotation carried out by the medium rotating means.

The isomer separation apparatus of the present invention is preferably arranged such that: the isomer separating means includes isomer inlets for receiving the respective isomers, and the respective isomer inlets are provided at positions corresponding to displacement amounts of the respective isomers between which displacement amounts a difference is caused by the difference in acceleration as time passes. The isomer separating means is not particularly limited. It is possible to use, as the isomer separating means, an apparatus for absorbing an isomer, an apparatus for detecting the isomer (an isomer detecting section), and a substance for absorption or adsorption, etc. of the isomer.

As described earlier, the respective isomer inlets are provided at the positions corresponding to displacement amounts of the respective isomers between which displacement amounts a difference is caused by the difference in acceleration as time passes. This allows an isomer separation in a simpler arrangement.

The embodiments and concrete examples of implementation discussed in the aforementioned detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICABILITY

As described earlier, the present invention is capable of separating isomers by a method which requires no contact treatment and no chemical reaction.

The invention claimed is:

1. An isomer separation method for a chiral substance, comprising:
   irradiating the chiral substance which is a mixture of different isomers, with circularly polarized light or elliptically polarized light, so as to cause a difference in radiation force between the different isomers; and
   separating the different isomers in accordance with a difference in acceleration between the different isomers, the difference in acceleration being caused by the difference in radiation force.

2. The isomer separation method as set forth in claim 1, wherein the chiral substance exists under vacuum or in a fluid medium containing a gas.

3. The isomer separation method as set forth in claim 1, wherein the circularly polarized light or elliptically polarized light has a frequency causing resonance at an electronic excitation level of any one of the different isomers included in the chiral substance.

4. The isomer separation method as set forth in claim 1, wherein:
   the chiral substance is irradiated with two beams of the circularly polarized light or elliptically polarized light which rotate in different directions; and
   one and the other of the two beams are emitted from (i) a given direction and (ii) a direction different from the given direction, respectively.

5. An isomer separation apparatus for a chiral substance, comprising:
   circularly polarized light irradiating means for irradiating the chiral substance which is a mixture of different isomers, with circularly polarized light or elliptically polarized light, so as to cause a difference in radiation force between the different isomers; and
   isomer separating means for separating at least one of the different isomers from the chiral substance in accordance with a difference in acceleration between the different isomers of the chiral substance, the difference in acceleration being caused by the difference in radiation force.

6. The isomer separation apparatus as set forth in claim 5, wherein the chiral substance exists under vacuum or in a fluid medium containing a gas.

7. The isomer separation apparatus as set forth in claim 5, wherein the light emitted by the circularly polarized light irradiating means has a frequency causing resonance at an electronic excitation level of any one of the different isomers included in the chiral substance.

8. The isomer separation apparatus as set forth in claim 5, wherein:
the circularly polarized light irradiating means irradiates the chiral substance with two beams of the circularly polarized light or elliptically polarized light which rotate in different directions; and
one and the other of the two beams are emitted from (i) a given direction and (ii) a direction different from the given direction, respectively.

9. The isomer separation apparatus as set forth in claim 5, further comprising:
chiral substance releasing means for unidirectionally releasing the chiral substance into the medium,
the circularly polarized light irradiating means emitting the light from a direction which intersects with the direction into which the chiral substance is released.

10. The isomer separation apparatus as set forth in claim 5, further comprising:
medium rotating means for rotating the fluid medium containing the chiral substance,
the circularly polarized light irradiating means emitting the light from a direction which intersects with a radius vector rotation plane of the rotation carried out by the medium rotating means.

11. The isomer separation apparatus as set forth in claim 5, wherein:
the isomer separating means includes isomer detecting sections for detecting the respective isomers; and
the respective isomer detecting sections are provided at positions corresponding to displacement amounts of the respective isomers between which displacement amounts a difference is caused by the difference in acceleration as time passes.

12. The isomer separation apparatus as set forth in claim 5, wherein:
the isomer separating means includes isomer inlets for receiving the respective isomers, and
the respective isomer inlets are provided at positions corresponding to displacement amounts of the respective isomers between which displacement amounts a difference is caused by the difference in acceleration as time passes.

13. The isomer separation apparatus as set forth in claim 12 wherein the isomer separating means further includes isomer detecting sections respectively provided in the vicinities of the isomer inlets, for detecting the respective isomers.

* * * * *